United States Patent
Albertson et al.

(10) Patent No.: US 9,055,984 B2
(45) Date of Patent: Jun. 16, 2015

(54) STERNAL RECONSTRUCTION SYSTEM

(75) Inventors: Thomas Albertson, Phoenixville, PA (US); Christopher Goheen, New Cumberland, PA (US); Mark Michels, Glen Mills, PA (US)

(73) Assignee: DePuy Synthes Products, Inc., Raynham, MA (US)

( * ) Notice: Subject to any disclaimer, the term of this patent is extended or adjusted under 35 U.S.C. 154(b) by 1995 days.

(21) Appl. No.: 11/152,738

(22) Filed: Jun. 13, 2005

(65) Prior Publication Data

US 2005/0240191 A1   Oct. 27, 2005

Related U.S. Application Data

(63) Continuation-in-part of application No. 10/830,130, filed on Apr. 21, 2004, now Pat. No. 7,704,252.

(51) Int. Cl.
| | | |
|---|---|---|
| *A61B 17/82* | (2006.01) | |
| *H01R 43/04* | (2006.01) | |
| *A61B 17/80* | (2006.01) | |
| *A61B 17/84* | (2006.01) | |
| *A61B 17/88* | (2006.01) | |
| *A61B 17/86* | (2006.01) | |

(52) U.S. Cl.
CPC .......... *A61B 17/8076* (2013.01); *A61B 17/823* (2013.01); *A61B 17/842* (2013.01); *A61B 17/864* (2013.01); *A61B 17/8861* (2013.01); *A61B 17/8869* (2013.01)

(58) Field of Classification Search
USPC ............. 606/60, 74, 263, 304, 323; 140/105, 140/106; 29/861, 862, 863, 865, 866
See application file for complete search history.

(56) References Cited

U.S. PATENT DOCUMENTS

| | | |
|---|---|---|
| 3,037,619 A | 6/1962 | Stevans |
| 3,187,752 A | 6/1965 | Glick |
| 4,682,849 A | 7/1987 | Kowata et al. |
| 4,880,002 A | 11/1989 | MacGregor |
| 4,889,110 A | 12/1989 | Galline et al. |
| 4,944,753 A | 7/1990 | Burgess et al. |
| 4,966,600 A | 10/1990 | Songer et al. |
| 5,061,827 A * | 10/1991 | Grabbe ............... 174/75 C |

(Continued)

FOREIGN PATENT DOCUMENTS

| | | |
|---|---|---|
| CN | 101198285 | 6/2008 |
| DE | 19628147 | 1/1998 |

(Continued)

OTHER PUBLICATIONS

International Patent Application No. PCT/US2005/13599: International Search Report dated Oct. 3, 2006, 1 page.

(Continued)

*Primary Examiner* — David Bates
*Assistant Examiner* — Michael Araj
(74) *Attorney, Agent, or Firm* — Baker & Hostetler LLP

(57) ABSTRACT

A sternal reconstruction system for securing parts of a sternum includes at least one flexible cable with a fused end fitting, at least one parallel fitting piece and at least one ferrule. Optionally, the system includes at least one cannulated screw. Circumferential or parasternal fixation may be brought about by use of the sternal reconstruction system. Also provided is a method for sternal reconstruction utilizing the sternal reconstruction system. Also provided is a kit for sternal reconstruction.

43 Claims, 9 Drawing Sheets

(56) References Cited

U.S. PATENT DOCUMENTS

| | | | |
|---|---|---|---|
| 5,190,545 A | 3/1993 | Corsi et al. | |
| 5,318,566 A * | 6/1994 | Miller | 606/60 |
| 5,320,663 A | 6/1994 | Cunningham | |
| 5,345,663 A | 9/1994 | Scruggs | |
| 5,361,475 A | 11/1994 | Scruggs | |
| 5,415,658 A * | 5/1995 | Kilpela et al. | 606/300 |
| 5,423,821 A | 6/1995 | Pasque | |
| 5,607,429 A | 3/1997 | Hayano et al. | |
| 5,649,927 A | 7/1997 | Kilpela et al. | |
| 5,653,711 A | 8/1997 | Hayano et al. | |
| 5,702,399 A | 12/1997 | Kilpela et al. | |
| 5,741,260 A * | 4/1998 | Songer et al. | 606/74 |
| 5,766,218 A | 6/1998 | Arnott | |
| 5,772,663 A * | 6/1998 | Whiteside et al. | 606/74 |
| 5,785,712 A | 7/1998 | Runciman et al. | |
| 5,810,825 A | 9/1998 | Huebner | |
| 5,908,421 A * | 6/1999 | Beger | 606/74 |
| 5,928,237 A * | 7/1999 | Farris et al. | 606/74 |
| 5,964,769 A | 10/1999 | Wagner et al. | |
| 5,997,542 A | 12/1999 | Burke | |
| 6,120,505 A * | 9/2000 | Huebner | 606/74 |
| 6,158,437 A | 12/2000 | Vagley | |
| 6,296,643 B1 | 10/2001 | Hopf et al. | |
| 6,391,030 B1 * | 5/2002 | Wagner et al. | 606/74 |
| 6,436,123 B1 | 8/2002 | Magovern | |
| 6,544,267 B1 | 4/2003 | Cole et al. | |
| 6,682,533 B1 | 1/2004 | Dinsdale et al. | |
| 7,065,267 B2 | 6/2006 | Zhong et al. | |
| 7,604,643 B2 | 10/2009 | Ciccone et al. | |
| 7,704,252 B2 | 4/2010 | Albertson et al. | |
| 2002/0091391 A1 * | 7/2002 | Cole et al. | 606/72 |
| 2002/0165548 A1 | 11/2002 | Jutley | |
| 2004/0199169 A1 | 10/2004 | Koons et al. | |
| 2005/0017547 A1 | 1/2005 | Wingen | |
| 2005/0038428 A1 | 2/2005 | Kelman et al. | |
| 2005/0171547 A1 * | 8/2005 | Aram | 606/74 |
| 2010/0168804 A1 | 7/2010 | Albertson et al. | |

FOREIGN PATENT DOCUMENTS

| | | |
|---|---|---|
| EP | 0649636 | 4/1995 |
| EP | 1890625 | 2/2008 |
| JP | 8-500261 | 12/1985 |
| JP | 61-296188 | 12/1986 |
| JP | 2000-262546 | 9/2000 |
| JP | 2001-276084 | 10/2001 |
| JP | 2003-529395 | 10/2003 |
| JP | 2004-92869 | 3/2004 |
| WO | WO 93/18716 | 9/1993 |
| WO | WO 94/00065 | 1/1994 |
| WO | WO 96/41581 | 12/1996 |
| WO | WO 98/35623 | 8/1998 |
| WO | WO 01/05315 | 1/2001 |
| WO | WO 2005/104967 | 11/2005 |
| WO | WO 2006/135935 | 12/2006 |
| ZA | 2007/10215 | 11/2008 |

OTHER PUBLICATIONS

International Patent Application No. PCT/US2005/13599: International Preliminary Report on Patentability and Written Opinion dated Oct. 3, 2006, 4 pages.

International Patent Application No. PCT/US2006/023229: International Search Report dated Oct. 13, 2006, 4 pages.

International Patent Application No. PCT/US2006/023229: International Preliminary Report on Patentability and Written Opinion dated Dec. 17, 2007, 14 pages.

European Patent Application No. EP 05738787: Supplementary Partial European Search Report dated Dec. 10, 2009, 4 pages.

Chase, et al., "Internal Fixation of the Sternum in Median Sternotomy Dehiscence", Plast Reconstr Surg., May 1999, 103(6), 1667-1673.

* cited by examiner

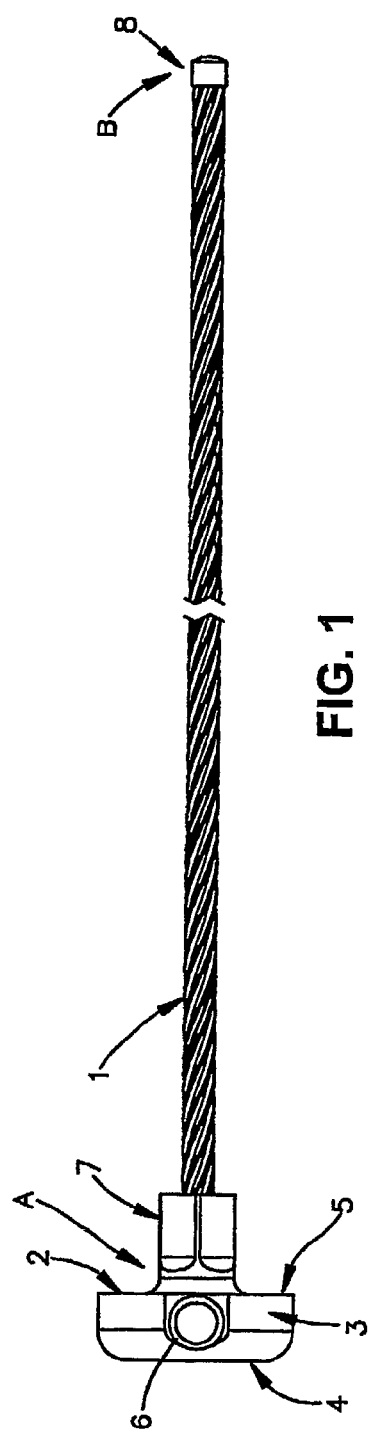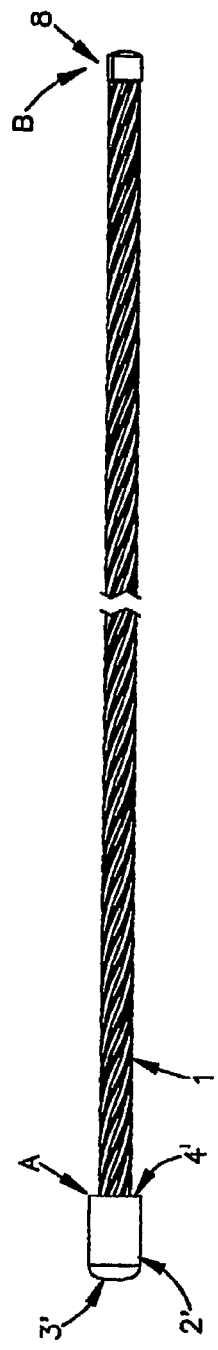
FIG. 1
FIG. 1A

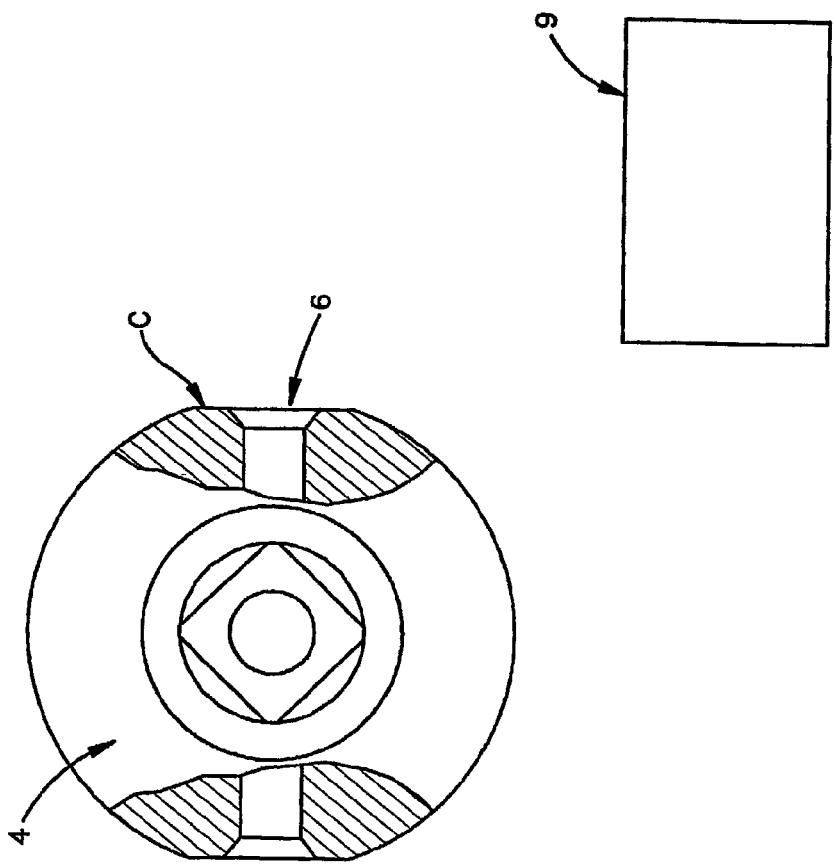
FIG. 2
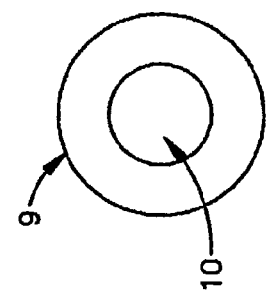
FIG. 3A
FIG. 3B

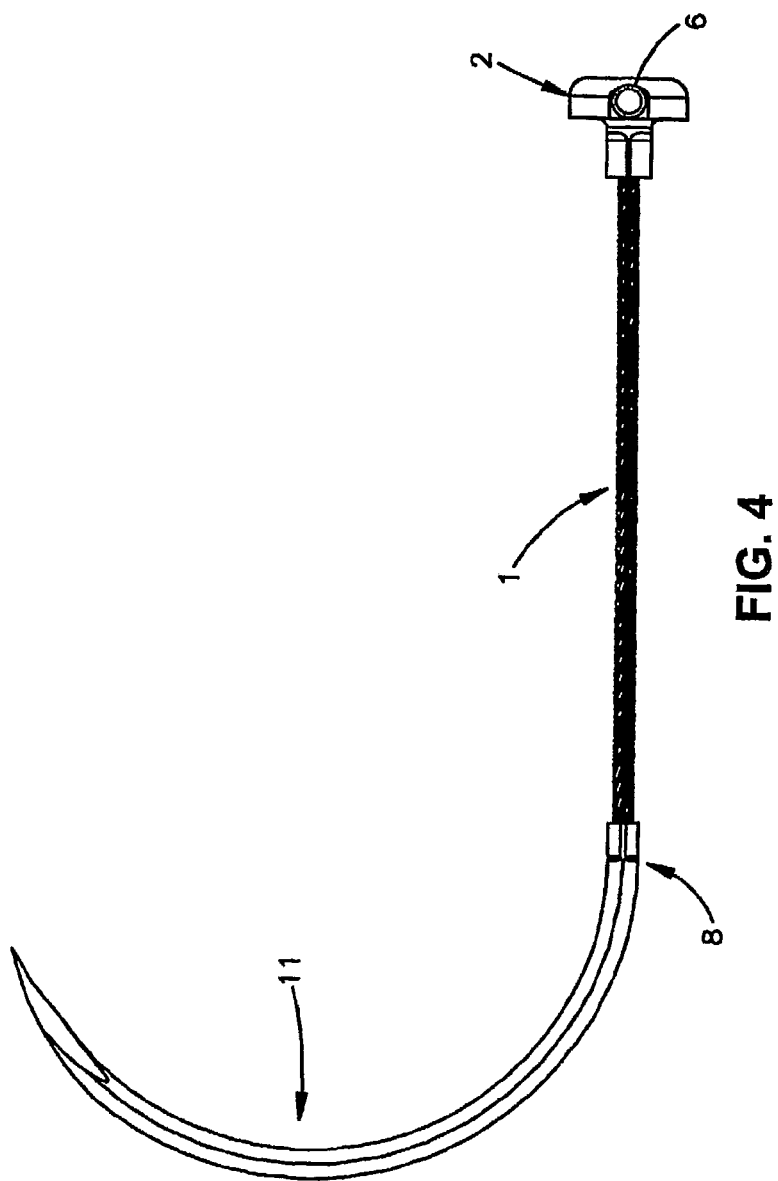

STERNAL RECONSTRUCTION SYSTEM

This application is a continuation-in-part of U.S. patent application Ser. No. 10/830,130, filed Apr. 21, 2004, now U.S. Pat. No. 7,704,252, issued Apr. 27, 2010, the entire disclosure of which is incorporated herein by reference.

FIELD OF THE INVENTION

The present invention relates generally to surgical reconstruction systems or devices, and more particularly, to devices for reapproximating two or more parts of a patient's sternum.

BACKGROUND OF THE INVENTION

Many surgical procedures require two or more parts of a sternum to be reapproximated, or fixed together, such as sternal reconstruction and repair of sternal trauma. In addition, various types of surgical procedures are currently performed to investigate, diagnose, and treat diseases involving tissues or organs located in a patient's thoracic cavity, such as the heart and lungs. These procedures typically require a partial or median sternotomy to gain access to the patient's thoracic cavity. A partial or median sternotomy is a procedure by which a saw or other appropriate cutting instrument is used to make a midline, longitudinal incision along a portion or the entire axial length of the patient's sternum, allowing two opposing sternal halves to be separated laterally. A large opening into the thoracic cavity is thus created, through which a surgeon may directly visualize and operate upon the heart and other thoracic organs, vessels, or tissues. Following the surgical procedure within the thoracic cavity, the two severed sternal halves must be reapproximated.

Various types of orthopedic devices are known for the reapproximation or fixation of bone fragments such as sternal halves. Such devices typically are used to stabilize bones by maintaining fractured bone portions in relatively fixed positions with respect to each other. The alignment and stability provided by the devices promotes the healing of fragments, allowing proper fusion to occur.

Internal fixation devices include bone screws, which are used in a variety of orthopedic applications for fixation of bone fragments. Bone fragments may be positioned in a desired configuration, and one or more holes may be drilled and tapped across the fracture. Compression and stabilization of the bone fragments may then be effected by screwing bone screws into the holes. One limitation associated with bone screws, however, is that repositioning or adjusting the bone screws following implantation is difficult. In order to accommodate a different alignment, it is often necessary to remove the original bone screws and drill new holes for subsequent bone screw implantation.

Metal pins also are often used to stabilize bones. Similar to bone screws, metal pins may be inserted in holes drilled across bone fragments to confer stability to the bone. However, as with bone screws, removal of the pins may be required if subsequent realignment of bone portions is necessary.

Bone plates are fastenable to the surface of a bone typically at both sides of a fracture to support and/or stabilize the fragments. Bone plates have typically been attached to the bone with bone screws that extend from the plate into the bone. In some examples, the head of the bone screw is locked to the plate (e.g., by threaded engagement between the screw head and the bone plate) and in other plates the head of the screw is free to angulate with respect to the plate, such that the screw may be placed in the bone at a surgeon-selected angle. In yet other examples, the screw head may cooperate with the bone plate to provide compression or distraction of the fragments (ie., to push the bone fragments towards or away from one another).

Intramedullary implants are another device used for fixation of bone fragments. Such a device may be placed in the central canal of a fractured bone and locked thereto at the longitudinal ends of the device using screws. The use of intramedullary implants is very invasive, though, and the implants are difficult to manipulate once installed within the canals of bone fragments.

External fixation devices also are commonly used to stabilize bone segments. These devices employ a plurality of pins which extend through a patient's skin into holes drilled in fractured bone. Clamps are used to secure the pins to a common apparatus, which may for example take the form of a rod that is disposed generally parallel to the anatomically correct longitudinal axis of the fractured bone. The clamps in combination with the common apparatus create a rigid frame for immobilizing the fracture to promote healing.

External skeletal fixation is a preferred method of treatment for various limb deformities, injuries, and other conditions including: severe open fractures, fractures associated with severe burns, fractures requiring distraction, fractures requiring limb lengthening, arthrodesis, infected fractures, and nonunions. External fixation offers several advantages over the above-mentioned internal fixation approaches. For example, external fixation enables skeletal stabilization to be managed from a location that is generally remote from the deformity, injury, or disease, thereby permitting direct surveillance of the limb and wound during related or subsequent procedures. In addition, external fixation facilitates adjustment of fracture alignment, bone lengthening, bone compression, and fixed distraction following initial surgery. Furthermore, minimal interference with proximal and distal joints allows immediate mobilization of a wounded limb, and insertion of the fixator pins can be performed under local anesthesia.

Despite these developments, there remains a need for fixation devices with improved adjustability and selectivity.

SUMMARY OF THE INVENTION

The present invention is directed to a sternal fixation device for securing parts of a sternum. The sternal reconstruction system for securing parts of a sternum comprises a flexible cable having first and second ends; a fused end fitting member; a parallel fitting piece; and a ferrule, wherein the first end of the cable comprises a fused end fitting member. In one embodiment the fused end fitting member is attached to the first end of the cable by crimping. Preferably the fused end fitting member comprises a preinstalled cylindrical end fitting having an upper surface and a lower surface, and having a diameter of from about 1 mm to about 5 mm and a length of from about 5 mm to about 20 mm, and is constructed from a material selected from the group consisting of titanium, alloys of titanium, stainless steel and resorbable materials.

In one embodiment the upper surface of the fused end fitting member has rounded edges and the lower surface of the fused end fitting member is flat. In another embodiment the lower surface of the fused end fitting member is designed to mate with an end surface of the parallel fitting piece.

In one embodiment the parallel fitting piece is a flattened cylindrical tube having a first end and a second end, a long cross-sectional axis and a short cross-sectional axis. Preferably the first and second ends of the parallel fitting piece are parallel to each other. In one embodiment at least one side having a long cross-sectional axis L is crimped along its length so as to provide two adjacent parallel channels through the parallel fitting piece. Preferably the parallel fitting piece is from about 3 mm to about 15 mm in length, the long cross-sectional axis is from about 3 mm to about 8 mm, and the short cross-sectional axis is from about 1 mm to about 5 mm.

In another embodiment the both sides of the parallel fitting piece having a long cross-sectional axis L are crimped along their lengths so as to provide two adjacent parallel channels through the parallel fitting piece, and the channels have the same aperture and cross-section. Preferably each channel has a diameter of from about 0.7 mm to about 2.5 mm. Preferably the parallel fitting piece is constructed from a material selected from the group consisting of, titanium, alloys of titanium, stainless steel and resorbable materials.

In another embodiment, the sternal reconstruction system of the invention further comprises at least one cannulated screw. The at least one cannulated screw may be a locking or a non-locking screw, and may be at least partially threaded for attachment to bone. The at least one cannulated screw is constructed from a material selected from the group consisting of titanium, alloys of titanium, stainless steel and resorbable materials. In one embodiment, the head of the at least one cannulated screw comprises a head which comprises a hollow aperture which is sized and shaped so as to accommodate the fused end fitting member.

In another embodiment the present invention is directed to a method for sternal reconstruction, comprising the steps of passing a flexible cable having a first and a second end through one channel of a parallel fitting piece having two channels; wrapping the flexible cable around the sternum; passing the flexible cable through the second channel of the parallel fitting piece; tensioning the flexible cable to a desired tension; and securing the tensioned cable, wherein the first end of the flexible cable comprises a fused end fitting member, and is designed to mate with an end surface of the parallel fitting piece.

In another embodiment the present invention is directed to a method for sternal reconstruction, comprising the steps of attaching at least one cannulated screw into the sternum; feeding a flexible cable having a first and a second end through the lumen of the at least one cannulated screw; passing the flexible cable having a first and a second end through one channel of a parallel fitting piece having two channels; wrapping the flexible cable around the sternum; passing the flexible cable through the second channel of the parallel fitting piece; tensioning the flexible cable to a desired tension; and securing the tensioned cable, wherein the first end of the flexible cable comprises a fused end fitting member, and is designed to mate with an end surface of the parallel fitting piece.

In one embodiment the tensioned cable is secured by crimping a ferrule onto the flexible cable. In another embodiment the inner diameter of the ferrule comprises a sharp edge in order to facilitate the cutting of the flexible cable during crimping of the ferrule onto the flexible cable. The tensioned cable may be secured by crimping a ferrule onto the flexible cable, the ferrule being situated at one end of the parallel fitting piece and the fused end fitting member being situated at the other end of the parallel fitting piece.

In another embodiment the present invention is directed to a sternal reconstruction kit comprising at least one flexible cable; at least one parallel fitting piece; and at least one ferrule, wherein the first end of the flexible cable comprises a fused end fitting member, and is designed to mate with an end surface of the parallel fitting piece. In another embodiment, the sternal reconstruction kit further comprises at least one cannulated screw and/or at least one reconstruction plate.

In one embodiment the at least one flexible cable is attached to a suture. The inner diameter of the at least one ferrule comprises a sharp edge in order to facilitate the cutting of the flexible cable during crimping of the ferrule onto the flexible cable.

BRIEF DESCRIPTION OF THE DRAWINGS

Preferred features of the present invention are disclosed in the accompanying drawings, wherein similar reference characters denote similar elements throughout the several views, and wherein:

FIG. 1 is a perspective view of a first embodiment of a sternum reconstruction flexible cable with preinstalled flattened round crimp fitting;
FIG. 1A is a perspective view of a sternum reconstruction system with a preinstalled fused end fitting;
FIG. 2 is an end-view, partial cross-section of crimp fitting;
FIG. 3A is an end view of a cylindrical ferrule;
FIG. 3B is a side view of a cylindrical ferrule;
FIG. 4 is a side view of a flexible cable with crimp fitting at one end and a suture at the other end.

DETAILED DESCRIPTION OF THE PREFERRED EMBODIMENTS

Figure 1C:
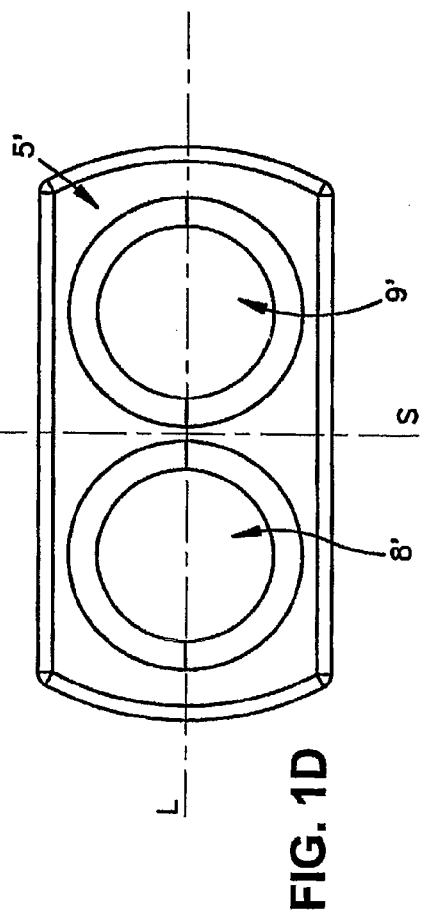
FIG. 1C is a partial side-view of a parallel fitting piece.

The sternal reconstruction system of the present invention comprises a flexible cable with crimp, optionally one or more cannulated screws and optionally one or more reconstruction plates. In one embodiment of the present invention, simple circumferential or parasternal fixation may be provided by use of a sternal reconstruction system comprising a flexible cable and ferrule. In another embodiment, fixation may be achieved by use of a sternal reconstruction system comprising a flexible cable, crimp and cannulated screws. In yet another embodiment, fixation may be achieved by use of a sternal reconstruction system comprising a flexible cable, crimp, cannulated screws and one or more reconstruction plates.

While various descriptions of the present invention are described in the Figures, it should be understood that the various features described are for illustrative purposes, and are exemplary only. Therefore, this invention is not to be limited to only the specifically preferred Figures depicted herein.

A first illustrative embodiment of a sternal reconstruction system is shown in FIGS. 1 to 3. The sternal reconstruction system shown in FIG. 1 comprises a flexible cable 1 having two ends, a first end A having attached thereto a crimp fitting 2, and a second end B consisting of a thermally fused end 8. Thermally fused end 8 may assist in threading flexible cable 1 through the other elements of the sternal reconstruction system, and may also assist in preventing unraveling of flexible cable 1. Flexible cable 1 can be a single strand wire or a multi-wire stranded cable having from about 2 to about 1000 strands, preferably from about 50 to about 300 strands and most preferably from about 110 to about 145 strands, and has first and second ends A, B. Flexible cable 1 may have any suitable degree of flexibility from highly flexible like yarn to stiff like wire. The flexible cable 1, however, is sufficiently flexible to readily conform to the sternum, while sufficiently rigid to be manipulated as required. Flexible cable 1 is typically attached to crimp fitting 2 by crimping the fitting onto the cable. Crimp fitting 2 may be constructed from any suitable bio-compatible material, including, but not limited to, titanium, alloys of titanium, stainless steel and resorbable materials, although one of ordinary skill in the art will know and appreciate that any biocompatible material may be used.

Crimp fitting 2 preferably comprises a preinstalled flattened disk-like crimp head 3 having an upper surface 4 and a lower surface 5. Upper surface 4 may be flat or curved and optionally has rounded edges. Lower surface 5 preferably is designed so as to mate with the top surface of a cannulated screw and/or a reconstruction plate, resulting in greater stability and/or a low profile. The flat lower surface 5 may assist in stabilizing the crimp fitting to a bone anchor, such as a screw, or to a bone plate, and results in greater stability of the system. In addition, the flat lower surface helps provide a low profile to the crimp fitting. Crimp head 3 has a diameter of from about 2 mm to about 10 mm, preferably about 6 mm, and a thickness of from about 0.1 mm to about 4 mm, preferably about 2 mm. While crimp head 3 is preferably a round disk, it may have other shapes such as square, rectangular or other polygon shape. Crimp head 3 has a diametrical hole or bore 6 through which the second or thermally fused end 8 of the flexible cable 1 is passed for attachment after the cable 1 is looped around the sternum. Diametric hole or bore 6 is sized so as to be able to accommodate the flexible cable 1, and preferably has a diameter of from about 0.7 mm to about 2.5 mm, and more preferably about 1 mm.

Crimp fitting 2 further comprises a crimp shaft 7 that extends generally perpendicular to lower surface 4. Crimp shaft 7 may be cylindrically shaped, or have a non-circular cross-section. The crimp shaft 7 may be a cylindrical tube which has an opening that receives the first end A of the flexible cable 1. The cylindrical tube may thereafter be crimped to attach the flexible cable 1 to the crimp fitting 2. The crimping process of the crimp shaft 7 may form a non-circular shape in the crimp shaft 7, or other desired shape. The crimp shaft 7 is located on the lower surface 4 of the crimp head such that the perimeter of the lower surface 4 of the crimp head surrounds the crimp shaft 7 in order to provide an annular bearing surface C. Annular bearing surface C has a width of from about 0.5 mm to about 3 mm. Preferably the crimp shaft 7 projects perpendicularly from the lower surface 4 of the crimp head 3. Crimp shaft 7 preferably is sized and shaped so as to fit within a cannulated screw or a bone plate. The non-circular cross-section of the crimp shaft 7 may engage the non-circular recess formed in a cannulated screw to prevent rotation of crimp fitting 2 in the cannulated screw. Crimp shaft 7 preferably may range in size from about 0.7 mm to about 4 mm in diameter, more preferably about 2.5 mm, and from about 1.5 mm to about 4 mm in length, more preferably about 3 mm. Preferably the diameter of crimp shaft 7 should not be less than the diameter of flexible cable 1. The length and shape of crimp shaft 7 may assist in stabilizing the crimp fitting 2 to a bone anchor, such as a screw, or to a bone plate, and results in greater stability of the system.

FIG. 2 shows an end view, partial cross-section of the upper face 4 of the crimp fitting 2. Diametric hole 6 may have an included counter sink region D on both sides of the crimp head 3 where it opens to the exterior. FIG. 3A shows an end view of a cylindrical ferrule 9 which contains a hole 10 along its longitudinal axis. FIG. 3B shows a side view of the ferrule. The hole 10 along the longitudinal axis of the ferrule 9 is sized so as to accommodate the flexible cable 1. The inner diameter of the ferrule 9 may have a sharp edge in order to facilitate the cutting of the flexible cable 1 during crimping of the ferrule 9 onto the flexible cable 1. Ferrule 9 may be constructed from any suitable bio-compatible material, including, but not limited to, titanium, alloys of titanium, stainless steel and resorbable materials, although one of ordinary skill in the art will know and appreciate that any biocompatible material may be used. In an illustrative embodiment, cylindrical ferrule 9 can be crimped onto the flexible cable 1 after flexible cable 1 is drawn through diametric hole 6 to a predetermined tension. The ferrule 9 preferably is sized so that it can not fit through the diametric hole 6, preferably at least after it is crimped onto the flexible cable 1. In another embodiment, ferrule 9 may be secured onto the flexible cable 1 by an adhesive. One of ordinary skill in the art will know and appreciate that any suitable biocompatible adhesive may be used. In another embodiment, flexible cable 1 and/or ferrule 9 are constructed from resorbable materials, and ferrule 9 may be secured onto the flexible cable 1 by thermal fusing.

Another illustrative embodiment of a sternal reconstruction system is shown in FIGS. 1A to 1D. In this embodiment, the sternal reconstruction system comprises a flexible cable 1 having two ends, a first end A having attached thereto a fused end fitting 2' and a second end B consisting of a thermally fused end 8. Fused end fitting 2' may be any suitable end fitting. Preferably fused end fitting member 2' is a tubular crimp fused end fitting. Flexible cable 1 is typically attached to fused end fitting 2' by crimping the fitting onto the cable. Fused end fitting 2' may be constructed from any suitable bio-compatible material, including, but not limited to, titanium, alloys of titanium, stainless steel and resorbable materials, although one of ordinary skill in the art will know and appreciate that any biocompatible material may be used.

Fused end fitting 2' is preferably a preinstalled cylindrical end fitting having an upper surface 3' and a lower surface 4'. Upper surface 3' may be flat or curved and optionally has rounded edges. Lower surface 4' preferably is designed so as to mate with an end surface of a parallel fitting piece 5', resulting in greater stability and/or a low profile. Fused end fitting 2' has a diameter of from 1 mm to about 5 mm, preferably about 2 mm, and a length of from about 5 mm to about 20 mm, preferably about 10 mm. While fused end fitting 2' is preferably either cylindrical or shaped so as to sit flush below the head of a cannulated screw 13, one of ordinary skill will know and appreciate that any suitable geometry may be used.

Figure 1B:
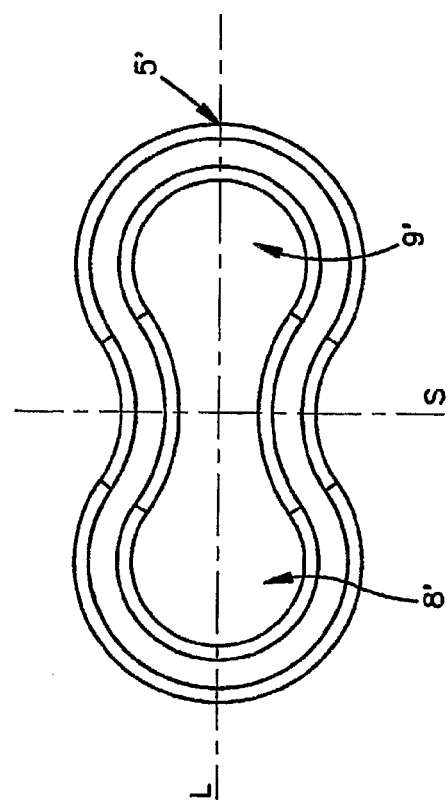
FIG. 1B is an end view of a parallel fitting piece.
Figure 1D:
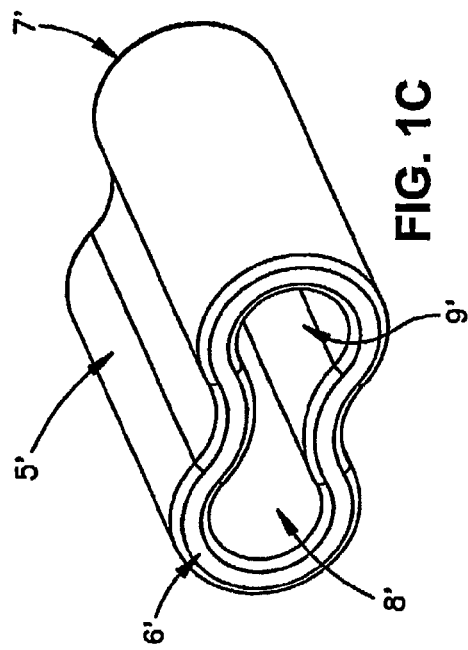
FIG. 1D is an end view of a parallel fitting piece.

Parallel fitting piece 5', shown in FIGS. 1B to 1D, may be a cylindrical tube which is flattened along its length perpendicular to first end 6' and a second end 7'. Parallel fitting piece 5' has a long cross-sectional axis L and a short cross-sectional axis S. Preferably, parallel fitting piece 5' has parallel ends 6' and 7'. One or both sides of end fitting 2' having a long cross-sectional axis L may be flat, but preferably at least one side having a long cross-sectional axis L is crimped along its length so as to provide at least two adjacent parallel channels through the parallel fitting piece. Parallel fitting piece 5' may range in length from about 3 mm to about 15 mm, preferably about 5 mm. Long cross-sectional axis L is from about 3 mm to about 8 mm, preferably about 4 mm, and short cross-ssectional axis S is from about 1 mm to about 4 mm, preferably about 2 mm. One of ordinary skill in the art will know and appreciate that any suitable dimensions may be used for the parallel fitting piece 5'. Preferably, the at least one side having a long cross-sectional axis L is crimped at the midpoint along its length so as to provide two adjacent parallel channels 8' and 9' having the same dimensions of aperture and cross-section. Most preferably, both sides having a long cross-sectional axis L are crimped at the midpoint along their lengths. The parallel channels 8' and 9' are sized so as to be able to accommodate the flexible cable 1, and preferably each has a diameter of from about 0.7 mm to about 2.5 mm, and more preferably about 1 mm. Parallel fitting piece 5' may be constructed from any suitable bio-compatible material, including, but not limited to, titanium, alloys of titanium, stainless steel and resorbable materials, although one of ordinary skill in the art will know and appreciate that any bio-compatible material may be used.

As shown in FIG. 1D, in an alternative embodiment parallel fitting piece 5' may be may be a cylindrical bar which is planed along its length perpendicular to first end 6' and a second end 7', on two opposite sides to form a cylindrical bar which has a long cross-sectional axis L and a short cross-sectional axis S. The planing of the two opposite sides along the length of the cylindrical bar may be carried out by mechanical methods such as standard machining and milling, although one of skill in the art will know and appreciate that any suitable method may be used. Preferably the cylindrical bar has a round cross-section, and, following planing, the cylindrical bar in cross-section is rectangular, with the two opposite sides along long cross-sectional axis L being parallel to one another, and the two sided along short cross-sectional axis S having rounded sides. However, one of ordinary skill in the art will know and appreciate that a cylindrical bar having any suitable geometry may be used. Parallel fitting piece 5' has at least two parallel channels which extend along its length perpendicular to first end 6' and a second end 7'. The parallel channels are preferably introduced into parallel fitting piece 5' by drilling, however one of ordinary skill in the art will know and appreciate that any suitable method may be used. Preferably, the at least two parallel channels are countersunk toward both the first end 6' and a second end 7' of parallel fitting piece 5'. Countersunk channels better accommodate the fused end fitting 2', resulting in a highly stable system. Parallel fitting piece 5' may range in length from about 3 mm to about 15 mm, preferably about 5 mm. Long cross-sectional axis L is from about 3 mm to about 8 mm, preferably about 4 mm, and short cross-sectional axis S is from about 1 mm to about 4 mm, preferably about 2 mm. One of ordinary skill in the art will know and appreciate that any suitable dimensions may be used for the parallel fitting piece 5'. Preferably, parallel fitting piece 5' has two adjacent parallel channels 8' and 9' having the same dimensions of aperture and cross-section. The parallel channels 8' and 9' are sized so as to be able to accommodate the flexible cable 1, and preferably each has a diameter of from about 0.7 mm to about 2.5 mm, and more preferably about 1 mm.

In another embodiment, parallel fitting piece 5' comprises two or more cylindrical bars or tubes which are attached together along their lengths perpendicular to first ends 6' and second ends 7'. Preferably the two or more cylindrical bars or tubes are attached together by welding, although one of ordinary skill in the art will know and appreciate that any suitable method may be used. Preferably, first ends 6' of each cylindrical bar or tube are aligned so as to provide a flat first end of parallel fitting piece 5'. Similarly, preferably second ends 7' of each cylindrical bar or tube are aligned so as to provide a flat second end of parallel fitting piece 5'. A channel is introduced into each cylindrical bar. Preferably, the channels are introduced by drilling, however one of ordinary skill in the art will know and appreciate that any suitable method may be used. Preferably, the channels are countersunk toward both the first ends 6' and second ends 7' of parallel fitting piece 5'. Parallel fitting piece 5' may range in length from about 3 mm to about 15 mm, preferably about 5 mm. Long cross-sectional axis L is from about 3 mm to about 8 mm, preferably about 4 mm, and short cross-sectional axis S is from about 1 mm to about 4 mm, preferably about 2 mm. One of ordinary skill in the art will know and appreciate that any suitable dimensions may be used for the parallel fitting piece 5'. Preferably, parallel fitting piece 5' has two adjacent parallel channels 8' and 9' having the same dimensions of aperture and cross-section. The parallel channels 8' and 9' are sized so as to be able to accommodate the flexible cable 1, and preferably each has a diameter of from about 0.7 mm to about 2.5 mm, and more preferably about 1 mm.

Thermally fused end 8 may be passed through either channel 8' or 9', and after cable 1 is looped around the sternum, thermally fused end 8 is passed through the other channel 8' or 9' for attachment. After the flexible cable is drawn through the parallel fitting piece 5' to a predetermined tension, lower surface 4' of fused end fitting 2' preferably is situated flush to, or mates with an end surface of a parallel fitting piece 5', resulting in greater stability and/or a low profile. In one embodiment, fused end fitting 2' may be attached to parallel fitting piece 5' by crimping the parallel fitting piece 5' onto the fused end fitting 2'. As described below, once the flexible cable 1 is drawn through the parallel fitting piece 5' to a predetermined tension, cylindrical ferrule 9 can be crimped onto the flexible cable 1 to secure the system. Preferably cylindrical ferrule 9 is crimped onto flexible cable 1 on one end of the parallel fitting piece 5', while the fused end fitting 2' is situated at the other end of the parallel fitting piece 5'. Without being bound by theory, it is believed that the sternal reconstruction system described above, comprising a parallel fitting piece 5' and a flexible cable 1, wherein the flexible cable 1 is secured by a fused end fitting 2' situated at the one end of the parallel fitting piece 5' and a cylindrical ferrule 9 crimped onto flexible cable 1 on the other end of the parallel fitting piece 5' after the flexible cable 1 is drawn to a predetermined tension, provides the benefits of an advantageous low profile, the system sitting flush to the sternum and improved tissue coverage.

Another illustrative embodiment of a sternal reconstruction system is shown in FIG. 4. In this embodiment, the second or thermally fused end 8 of the flexible cable 1 may be attached to a suture or needle 11. The suture 11 may typically be removed following its use, and is designed to be removed while preserving the fused end of the cable 1. The suture 11 may be constructed from any suitable bio-compatible material, including, but not limited to, titanium, alloys of titanium and stainless steel, although one of ordinary skill in the art will know and appreciate that any biocompatible material may be used.

The flexible cable 1 and crimp fitting 2 may be used to reapproximate, or secure together, two or more parts of a sternum by placing the crimp fitting 2 against a sternum to be mended and the flexible cable 1 wound around the separate portions of the sternum. The second or thermally fused end 8 of the flexible cable 1 to be attached to the crimp fitting 2 is pulled to bring the flexible cable 1 taut around the sternum, thus reapproximating the separated parts of the sternum. The second or thermally fused end 8 of the flexible cable 1 is passed through the diametrical hole 6, and the flexible cable 1 is pulled taut. The tensioning of the flexible cable 1 may be carried out, for example, by use of a safety cable tool. When the desired tension is achieved, the flexible cable 1 is secured in place by the ferrule 9. Attachment of the ferrule 9 to the flexible cable 1 may be carried out, for example, by crushing with pliers or any suitable crimping instrument. In an illustrative embodiment, a cylindrical ferrule 9 (FIG. 3) can be crimped onto the flexible cable 1 after the cable 1 is drawn through the hole 6 in crimp head 3 to a predetermined tension.

The flexible cable 1 has a diameter of from about 0.7 mm to about 2.5 mm. Typically, if the flexible cable 1 is constructed of non-resorbable materials, it has a diameter of from about 0.7 mm to about 1.5 mm. Preferably flexible cable 1 has a diameter of about 1 mm. In one embodiment of the invention the flexible cable is Cerclage wire. The flexible cable 1 may be of any suitable length, and is preferably from about 10 cm to about 1.5 m in length. Flexible cable 1 may be constructed from any suitable bio-compatible material, including, but not limited to, titanium, alloys of titanium, stainless steel and resorbable materials, although one of ordinary skill in the art will know and appreciate that any biocompatible material may be used.

Figure 5:
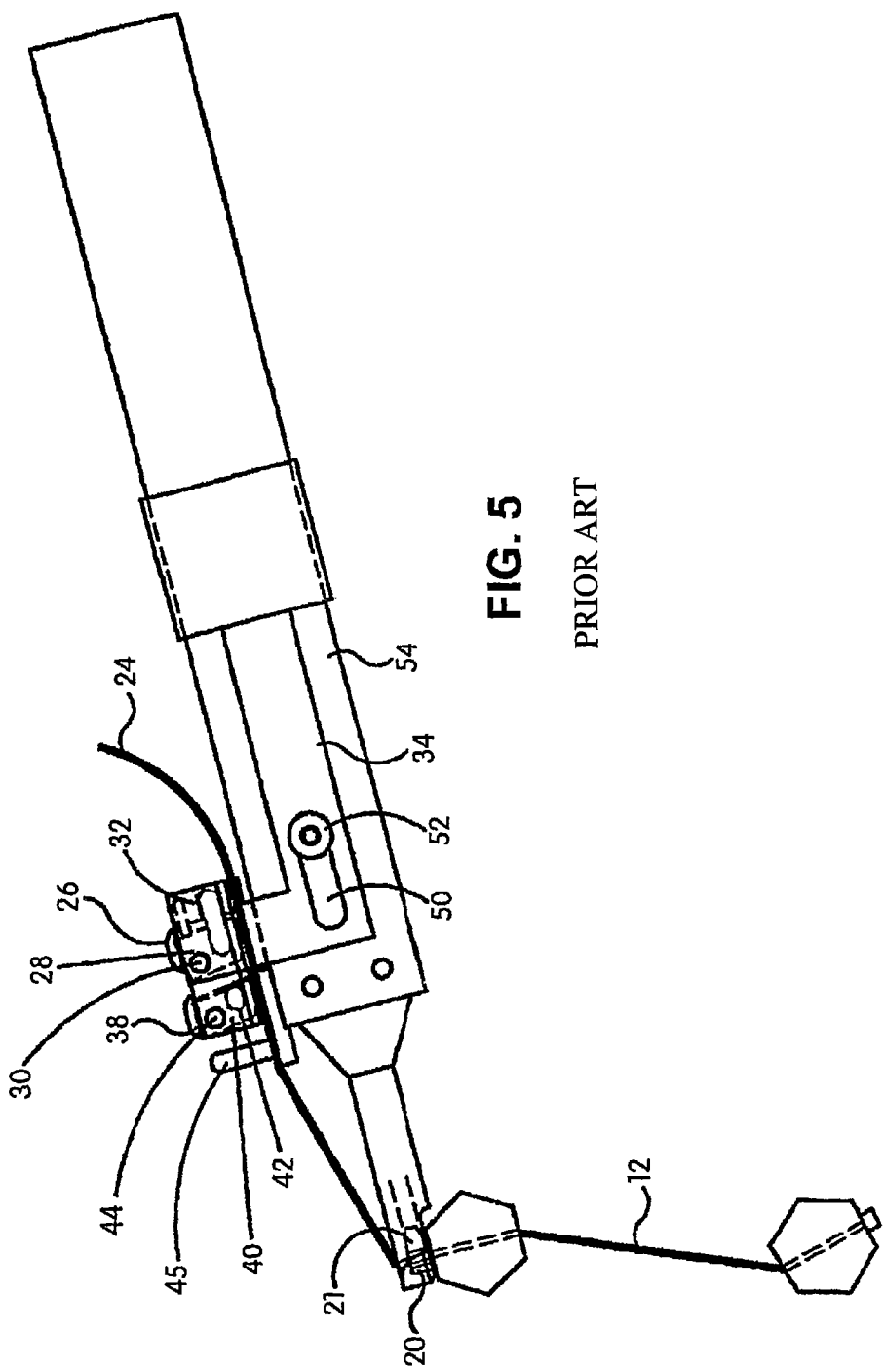
FIG. 5 is a perspective view of a safety cable tool.
Figure 6:
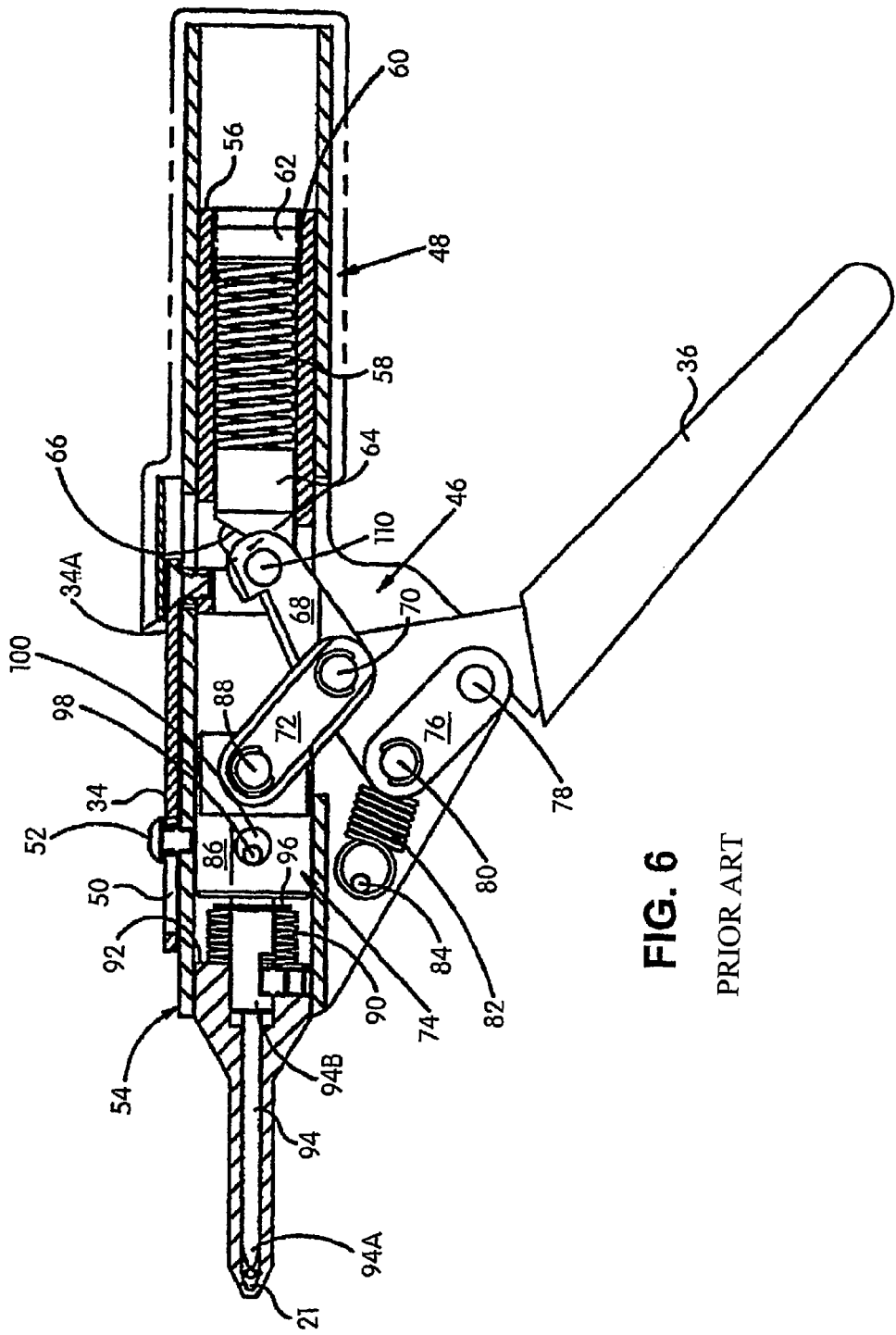
FIG. 6 is a cross-sectional view of a safety cable tool.

FIGS. 5 and 6 show a safety cable tool. The safety cable tool can be used for tensioning the flexible cable or wire 1 used with the sternal reconstruction system. The tool can be used to grasp and pull a flexible cable 1 to a predetermined tension limit. At the predetermined tension, the tool can be used to crimp a ferrule 9 to secure the flexible cable 1. The tool may also be used to sever the unused portion of flexible cable 1. The crimping and severing processes may be carried out independently or simultaneously, and manually or automatically. FIG. 5 shows a ferrule 20 seated in aperture 21 of the safety cable tool. A cable 12 with free end 24 is passed through the ferrule and through a clamping assembly 26 connected to a reciprocal arm 34. The cable 12 is also connected to a second clamping assembly 38. The clamping assemblies include pawls 28 and 40, which allow movement of the cable only in the direction of the cable's free end 24.

FIG. 6 shows an exploded perspective of the safety cable tool. Upon depression of handle 36 toward housing 54, handle 36 pivots about pin 80 and forces pin 70 to move upwards. As pin 70 goes up, arm 68 rotates clockwise about pin 110 and arm 72 rotates counterclockwise about pin 88, forcing pins 88 and 110 apart. Pin 110 is linked to reciprocal arm 34. As pin 110 moves away from pin 88, pressure is applied to move reciprocal arm 34 against the bias of spring 58, putting tension on cable 12. When the tension on cable 12 equals the bias of spring 58, pin 110 will move no farther and depressing handle 36 forces pin 88 to move toward the aperture 21. Pin 110 is also linked to a plunger 94 such that when pin 88 is forced in the direction of the aperture 21, plunger end 94A is pushed into aperture 21, thereby crimping the ferrule 20 about the cable 12 and simultaneously cutting cable 12 on the free end side of the ferrule. Suitable safety cable tools are commercially available from Daniels Manufacturing Corporation and are described in U.S. Pat. Nos. 5,320,663; 5,345,663; and 5,361,475, and U.S. patent application Publication No. U.S. 2004/0199169, the contents of which are incorporated herein in their entirety.

In one embodiment of the sternal reconstruction system, one end of the cable 1 comprises a preinstalled flattened round crimp fitting 2 with a diametrical hole 6 through which the second or thermally fused end 8 of the flexible cable 1 may pass after the cable 1 is looped around the sternum or passes through the cannulated screw 13. In this embodiment, the separated parts of the sternum may be reapproximated by tensioning the flexible cable 1 to a desired tension, and securing the cable 1 by crimping. In one embodiment, a cylindrical ferrule 9 may be crimped onto flexible cable 1 after the cable 1 is drawn through a cannulated screw and the diametric hole 6 in crimp fitting 2 to the preselected desired tension. The safety cable tool described above may be used to achieve such tensioning and crimping.

In another embodiment, the sternal reconstruction system comprises flexible cable 1 with fused end piece 2' and parallel fitting piece 5'. In this embodiment, the separated parts of the sternum may be reapproximated by passing the flexible cable through one channel of parallel fitting piece 5', looping flexible cable 1 around the sternum, passing it through the second channel of parallel fitting piece 5', tensioning the flexible cable 1 to a desired tension, and securing the cable 1 by crimping a cylindrical ferrule 9 onto the flexible cable 1. In another embodiment, the sternal reconstruction system comprises flexible cable 1 with fused end piece 2', parallel fitting piece 5' and one or more cannulated screws 13. A cylindrical ferrule 9 may be crimped onto flexible cable 1 after the cable 1 is drawn through one channel of parallel fitting piece 5', one or more cannulated screws and the second channel of parallel fitting piece 5' to the preselected desired tension. The safety cable tool described above may be used to achieve such tensioning and crimping.

Figure 7:
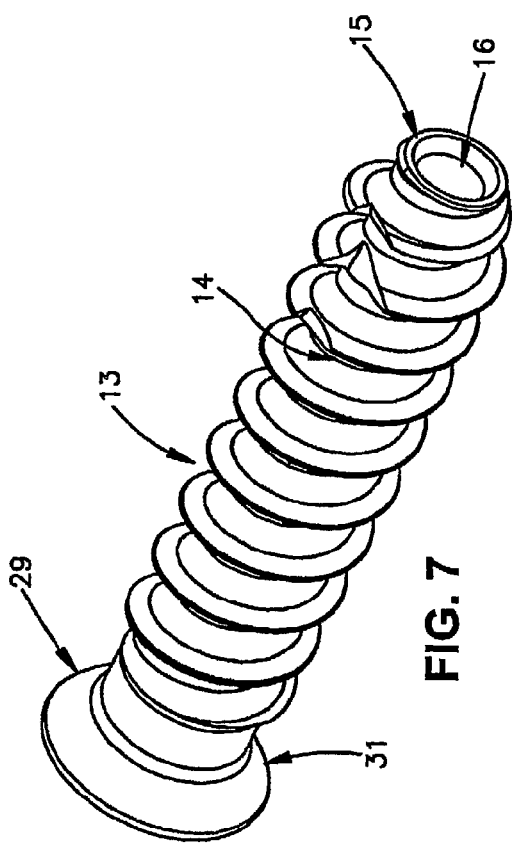
FIG. 7 is a top view of a cannulated screw.

In another illustrative embodiment, the sternal reconstruction system comprises flexible cable 1, crimp fitting 2 and at least one cannulated screw 13. FIG. 7 shows cannulated screw 13, having a shaft 14 that is at least partially threaded for attachment to bone. The length of shaft 14 and the shaft thread configuration is selected to be suitable for use in the sterna. As is well known in the art, the threads and a tip 15 can be made to be self-tapping and/or self-drilling to facilitate implantation. Shaft 14 has a diameter of from about 1 mm to about 5 mm, and is cannulated with a channel or throughbore 16 for receiving the flexible cable 1 to aid in fixation of the sternum. The diameter of throughbore 16 is preferably from about 0.7 mm to about 2.5 mm, and more preferably about 1 mm. The head 29 of the cannulated screw 13 preferably has a flat or curved under surface 31 which will bear against a reconstruction plate (if used) or the anterior side of the sternum.

Figure 8:
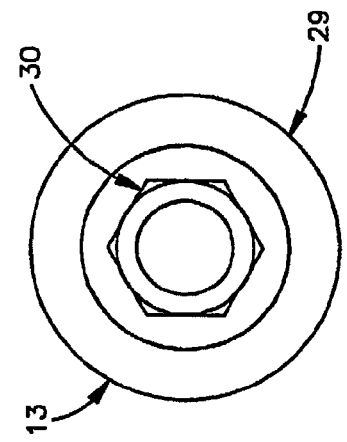
FIG. 8 is an end view of a cannulated screw.
Figure 9:
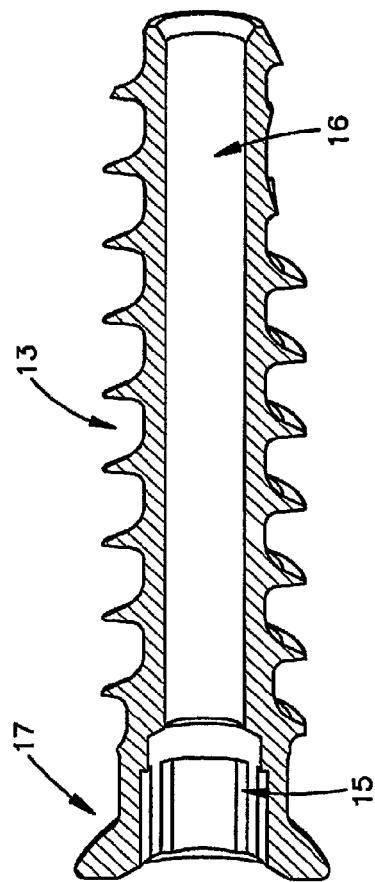
FIG. 9 is an exploded side view of a cannulated screw.

Further illustrative embodiment of a cannulated screw 13 are shown in FIGS. 8 and 9. As shown in FIG. 8, which shows an end view of cannulated screw 13, the head 29 of the cannulated screw 13 may comprise an internal hex 30 for receiving an installation tool. An installation tool for use in drilling a hole in bone and for driving any of a variety of cannulated fasteners into the drilled hole is further described in pending U.S. application Ser. No. 10/820,080 now U.S. Pat. No. 7,604,643 issued Oct. 20, 2009, entitled "Adjustable Tool for Cannulated Fasteners," by Ciccone et al., which is incorporated by reference herein in its entirety. The diameter of internal hex 30, measured as the distance between opposite faces, is from about 1.5 mm to about 4 mm, and more preferably about 2.5 mm. FIG. 9 shows a cross-sectional view of cannulated screw 13, and shows that the head 29 of the cannulated screw 13 comprises a hollow aperture 15, while the shaft of the cannulated screw 13 is cannulated with a throughbore 16 which may receive the flexible cable 1. The head 29 of the cannulated screw 13 has a top surface that may be curved, substantially flat or other complex geometry. In one embodiment, the lower surface 4 of the crimp fitting 2 has a geometry that compliments the top surface of the screw 13 or reconstruction plate 18 to assist in stabilizing the crimp fitting 2 in location on the screw 13 or reconstruction plate 18. The hollow aperture 15 is preferably sized and shaped so as to accommodate crimp shaft 7. The matching of the size and shape of crimp shaft 7 to the hollow aperture 15 may result in greater stability of the crimp fitting 2 in the screw 13, particularly if there is a close fit between the shaft 7 and aperture 15. In this manner the crimp shaft 7 may act as a journal inside the screw aperture 15. The flat lower surface 5 of the crimp fitting 2 preferably sits flush to the head of the cannulated screw 13, and also provides stability to the system. In another embodiment, fused end fitting 2' has a geometry that compliments the top surface of the screw 13 or reconstruction plate 18 to assist in stabilizing the fused end fitting 2' in location on the screw 13 or reconstruction plate 18. The hollow aperture 15 is preferably sized and shaped so as to accommodate fused end fitting 2'. The matching of the size and shape of fused end fitting 2' to the hollow aperture 15 may result in greater stability of the fused end fitting 2' in the screw 13. Fused end fitting 2' preferably sits flush below the head of the cannulated screw 13, and also provides stability to the system. In general, any surgical screw as described above, having a threaded or a non-threaded head 17 of an appropriate size and geometry for select plate holes of the bone plate can be used. The head 29 of cannulated screw 13 may be configured to lock with an optimally supplied bone plate or to be a non-locking screw. The head 29 of cannulated screw 13 has a diameter of from about 2 mm to about 10 mm, and preferably about 6 mm.

The cannulated screws 13 may be constructed from any suitable bio-compatible material, including, but not limited to, titanium, alloys of titanium, stainless steel and resorbable materials, although one of ordinary skill in the art will know and appreciate that any biocompatible material may be used. The cannulated screws 13 may be of any suitable length, and are typically from about 5 mm to about 24 mm in length. The skilled artisan will know that a screw 13 should be selected preferably so as to have a length such that, on use in sternal reconstruction, the tip of screw 13 will extend up to the posterior surface of the sternum, but preferably will not protrude to an undesirable distance from the posterior of the sternum.

In one embodiment of the invention, the cannulated screws 13 are inserted into the sternum on opposite sides of the sternal fragments. Flexible cable or wire 1 is fed through the lumen 16 of the cannulated screws 13, and is tensioned to a desired tension, causing the portions of the sternum to be brought together. The tensioned flexible cable 1 is secured to secure the aligned sternum. The cannulated screws 13 prevent the flexible cable or wire 1 from bearing directly on the soft bone of the sternum, thus alleviating the clinical problems of "cut through" and sternal dehiscence, or separation of the bony sternum and manubrium following median sternotomy.

Figure 10:
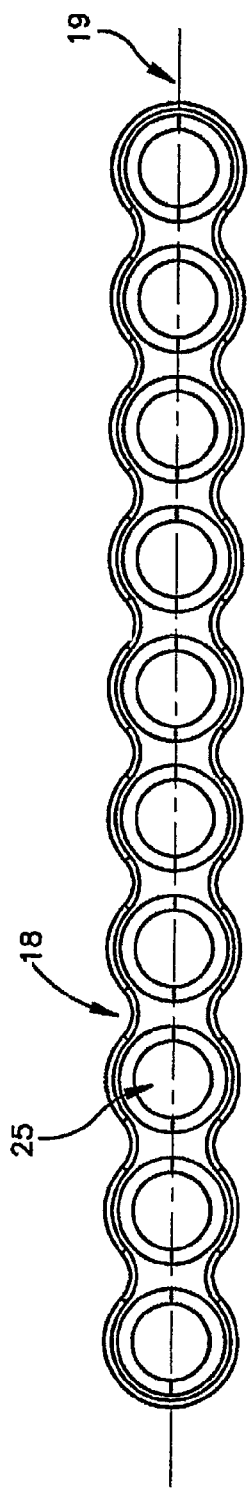
FIG. 10 is an overhead view of a reconstruction plate.

In another illustrative embodiment, the sternal reconstruction system comprises flexible cable 1, crimp fitting 2, cannulated screws 13 and at least one bone reconstruction plate 18. FIGS. 10 to 13 show illustrative embodiments of the reconstruction plate 12. FIG. 10 shows a top view of reconstruction plate 18, having a generally rectangular cross section. However, any suitable configuration for the reconstruction plate 18 could be used. The reconstruction plate 18 has a longitudinal axis 19, upper and lower surfaces 22, 23, at least one plate hole 25 disposed generally perpendicularly to the longitudinal axis 19 of the reconstruction plate 18, and at least one plate hole or bore 26 disposed transverse to the generally perpendicularly disposed plate hole 25. Generally perpendicular plate holes 25 are each independently angled at a solid angle of from 0° to about 30° from normal to the upper and lower surfaces of the plate 18. Preferably, perpendicular plate holes 25 are each independently angled at an angle of from 0° to about 30° from normal to the upper and lower surfaces of the plate 18 and along longitudinal axis 19. Most preferably, generally perpendicular holes 25 are normal to the upper and lower surfaces of the plate 18, i.e., at 0°. Transverse plate holes or bores 26 are each independently angled at a solid angle of from 0° to about 30° from normal to the side surfaces of the plate 18. Preferably, transverse plate holes or bores 26 are each independently angled at an angle of from 0° to about 30° from normal to the side surfaces of the plate 18 and transverse to longitudinal axis 19. Most preferably, transverse holes or bores 26 are normal to the side surfaces of the plate 18, ie., at 0°. Reconstruction plate 18 has a length of from about 30 mm to about 250 mm, more preferably from about 80 mm to about 200 mm; a width of from about 5 mm to about 20 mm, more preferably from about 6 mm to about 10 mm; and a thickness of from about 0.5 mm to about 10 mm, more preferably from about 2 mm to about 4 mm. Plate holes 25 extend from the upper surface 22 through the lower surface 23 of the reconstruction plate, and can be optionally used for accommodating fasteners, e.g. cannulated screws 13, pins, and/or flexible cable 1, to secure the reconstruction plate 18 to the sternum.

Plate holes 26 extend transversely through the longitudinal axis 19 of the reconstruction plate 18, and can optionally also be used for accommodating fasteners, e.g. cannulated screws and/or flexible cable, to secure the reconstruction plate to the sternum. The transverse holes 26 are preferably located between generally perpendicular holes 25. Any suitable combination of fasteners, such as, for example, cannulated screws 13 or other screws, blades, nails, pins, etc. may be used to secure the reconstruction plate 18 to the sternum; for example, in one embodiment, bone anchors may be used solely with the generally perpendicular plate holes 25, while in another embodiment flexible cable such as cable 1 and crimp fitting 2 solely may be used with the transverse plate holes 25. In a preferred embodiment, the reconstruction plate 18 comprises a plurality of plate holes 25 preferred embodiment, a combination of generally perpendicular and transverse plate holes 25, 26 is selected so as to give optimum local securing of the reconstruction plates 18. In a preferred embodiment, the reconstruction plate 18 comprises a plurality of plate holes 25 disposed generally perpendicularly to the longitudinal axis 19 of the reconstruction plate 18, and a plurality of plate holes 26 disposed transverse to the generally perpendicularly disposed plate holes 25.

Figure 11:
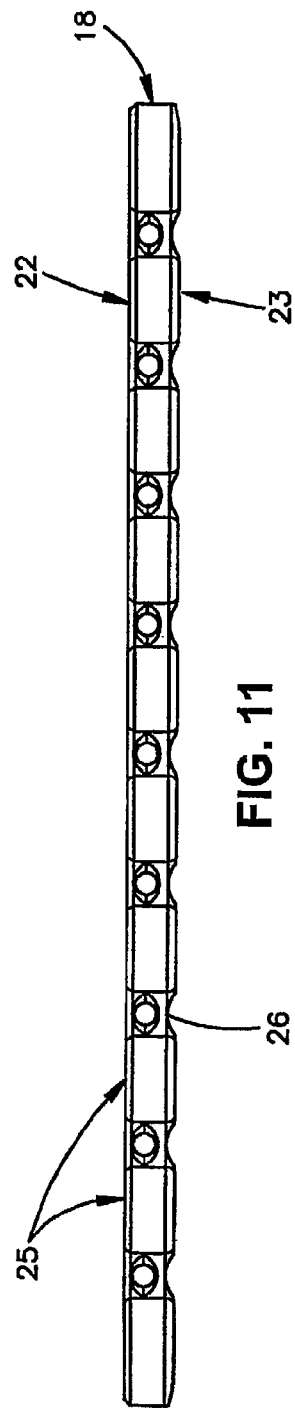
FIG. 11 is a side view of a reconstruction plate.
Figure 12:
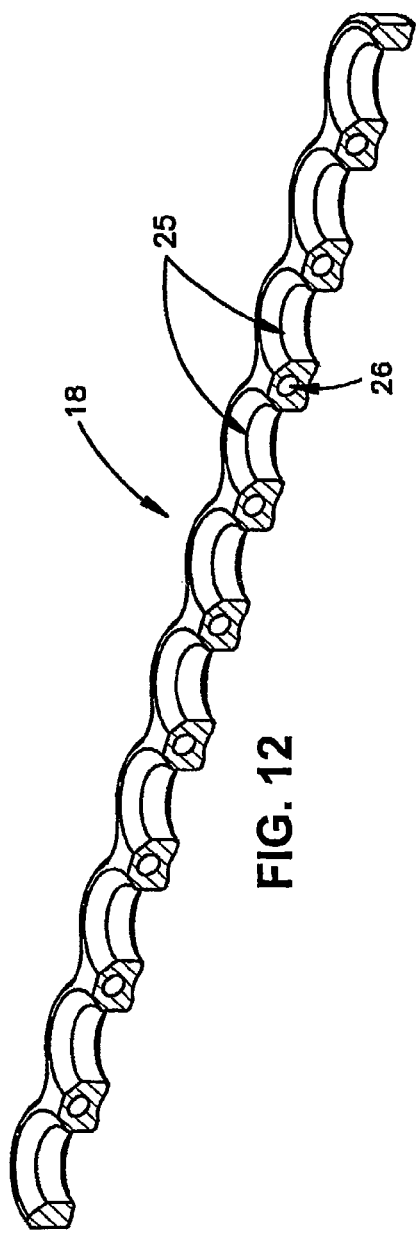
FIG. 12 is a cross-sectional view of a reconstruction plate.
Figure 13:
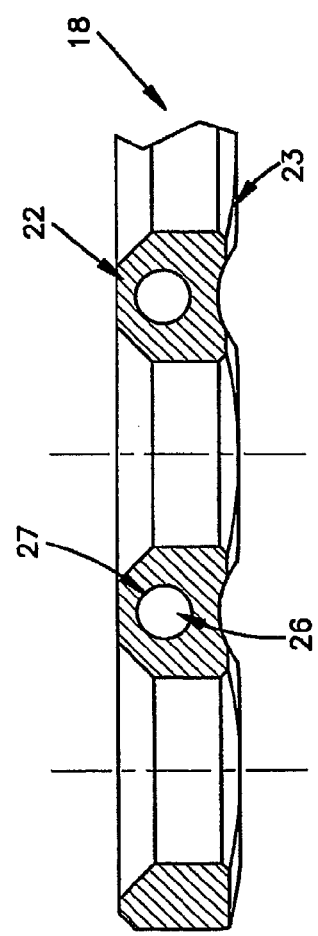
FIG. 13 is a partial side view of a reconstruction plate.

The reconstruction plates 18 may be constructed from any suitable bio-compatible material, including, but not limited to, titanium, alloys of titanium, stainless steel, resorbable materials, radio-translucent materials, allograft materials and resorbable materials, although one of ordinary skill in the art will know and appreciate that any biocompatible material may be used. The reconstruction plates 18 may comprise a plurality of generally perpendicular plate holes 25 which pass through the upper and lower surfaces of plate 18 and are generally perpendicular to the longitudinal axis for receiving bone anchors. The reconstruction plates 18 may further comprise a plurality of holes or bores 26 disposed generally transversely to the generally perpendicularly disposed plate holes 25. Typically, the reconstruction plates 18 comprise from about 2 to about 26 generally perpendicular plate holes 25 and from about 1 to about 25 transverse holes or bores 26. As shown in FIG. 10, an overhead view of the reconstruction plate 18, the generally perpendicular plate holes 25 are generally uniform in shape and size, and preferably are circular holes with a diameter of from about 2 mm to about 9 mm, more preferably from about 4 mm to about 6 mm. In another embodiment the holes may be oblong and may be ramped to provide compression. The generally perpendicular plate holes may be configured to lock with an optionally supplied bone fastener. In FIG. 11, which shows a side view of reconstruction plate 18, the transverse plate holes 26 are disposed between adjacent generally perpendicular plate holes 25. FIG. 12 shows a cross-sectional view of reconstruction plate 18, wherein the location of the transverse plate holes 26 between adjacent generally perpendicular holes 25 can be seen. Transverse plate holes 26 typically have a diameter smaller than that of the generally perpendicular holes 25. Preferably, the transverse plate holes 26 have a diameter of from about 0.7 mm to about 2.5 mm, and more preferably about 1 mm. The diameter of the transverse plate holes 26 preferably is selected so as to accommodate the flexible cable 1. Typically, the reconstruction plate 18 is counter-bored at the location of each transverse hole 26. FIG. 13 shows a side view of a reconstruction plate 18, with transverse hole 26 and counter-bore 27.

As shown in FIGS. 10 to 13, both the generally perpendicular plate holes 25 and transverse plate holes 26 may be round and cylindrical. This preferred geometry minimizes the change in material properties in the areas near the plate holes. In one embodiment, generally perpendicular plate holes 25 are countersunk toward either the upper or the lower surface 22, 23 of the reconstruction plate 18. In a preferred embodiment, the generally perpendicular plate holes 25 are countersunk toward both the upper and the lower surface 22, 23 of the reconstruction plate 18. Countersunk generally perpendicular plate holes 25 better accommodate the heads of the cannulated bone screws 13, resulting in a highly stable system. In a preferred embodiment, the countersinks are in the shape of a cone.

In one embodiment the upper and lower surfaces 22, 23 of the reconstruction plate 18 are planar. Because of the symmetry of the bone plate 18, the bone plate 18 can be attached with either upper or lower surface 22, 23 facing the bone with identical clinical results. In a preferred embodiment, at least one reconstruction plate 18 is attached to the sternum on opposite sides of the sternal fragments.

The use of flexible cable 1, reconstruction plates 18 and cannulated screws 13 may be necessary in more complicated sternal reconstruction procedures, such as procedures wherein both midline and transverse fractures must be addressed. The reconstruction plates 18 can be attached to each side of the split sternum by cannulated screws 13. Flexible cable or wire 1 may then be used to align and reduce the sternum. If transverse fractures are present, the reconstruction plates 18 function to reduce such fractures. Without being bound by theory, it is believed that the cannulations 16 in the screw 13 and the transverse holes 26 in the reconstruction plates 18 provide improvements to the Chase technique, which is described in "Internal Fixation of the Sternum in Median Sternotomy Dehiscence," Chase et al., Plastic and Reconstructive Surgery, May 1999, the contents of which are incorporated herein as if fully set forth.

In one embodiment, one end of the flexible cable 1 comprises a preinstalled flattened round crimp fitting 2 with a diametrical hole or bore 6 through which the second or thermally fused end 8 of the flexible cable 1 may pass after the flexible cable 1 is looped around the sternum or passes through the cannulated screws 13 and/or through the reconstruction plates 18 and throughbores 16 of the cannulated screws 13. In this embodiment, the separated parts of the sternum may be reapproximated by tensioning the flexible cable 1 to a desired tension, and securing the flexible cable 1 by crimping. In one embodiment, a cylindrical ferrule 9 may be crimped onto flexible cable 1 after the cable 1 is drawn through the hole 6 in crimp fitting 2 to the preselected desired tension. The safety cable tool described above may be used to achieve such tensioning and crimping.

The present invention also relates to a sternal reconstruction kit which comprises at least one flexible cable 1; at least one parallel fitting piece 5'; and at least one ferrule 9, wherein the first end of the flexible cable comprises a fused end fitting member, and is designed to mate with an end surface of the parallel fitting piece. Optionally the kit may contain at least one flexible cable 1, wherein the second or thermally fused end 8 of the flexible cable 1 may be attached to a suture 11. Further, the kit may optionally comprise a plurality of sizes of cannulated screws 13 and/or a plurality of sizes of reconstruction plates 18. The inner diameter of the ferrule 9 may have a sharp edge in order to facilitate the cutting of the flexible cable 1 during crimping of the ferrule 9 onto the flexible cable 1.

While various descriptions of the present invention are described above, it should be understood that the various features can be used singly or in any combination thereof. Therefore, this invention is not to be limited to only the specifically preferred embodiments depicted herein. Further, it should be understood that variations and modifications within the spirit and scope of the invention may occur to those skilled in the art to which the invention pertains. For example, fixation of a sternum may be effected by use of a flexible cable 1 with fused end piece 2' and parallel fitting piece 5', and/or in combination with cannulated screws 13 and/or further in combination with sternal reconstruction plates 18. Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

What is claimed is:

1. A sternal reconstruction system for securing parts of a sternum comprising:
  a flexible cable having opposed first and second ends;
  an end fitting member attached to the first end of the flexible cable, the end fitting member having a cross-sectional dimension greater than that of the flexible cable;
  a fitting piece having a first end, a second end opposite the first end of the fitting piece, a length measured from the first end of the fitting piece to the second end of the fitting piece, and a first channel and a second channel each extending substantially parallel through the fitting piece along an entirety of the length from the first end of the fitting piece to the second end of the fitting piece; and
  a ferrule including a first end and a second end opposite the first end of the ferrule, the ferrule defining a hole that is sized to receive the flexible cable, the first end of the ferrule defining a first opening of the hole, the second end of the ferrule defining a second opening of the hole, the ferrule including a sharp edge positioned within the hole, such that the sharp edge is configured to cut the flexible cable during crimping of the ferrule onto the flexible cable;
  wherein the sternal reconstruction system defines an assembled configuration in which: 1) the end fitting member abuts the first end of the fitting piece at a first location aligned with the first channel, and 2) the ferrule is crimped to the flexible cable such that the first end of the ferrule abuts the second end of the fitting piece at a second location and the first opening of the hole faces and overlaps with the second channel.

2. The sternal reconstruction system of claim 1, wherein the end fitting member is fused and attached to the first end of the cable by crimping.

3. The sternal reconstruction system of claim 2, wherein the end fitting member comprises a preinstalled cylindrical end fitting having an upper surface a lower surface, and a diameter of from about 1 mm to about 5 mm and a length of from about 5 mm to about 20 mm.

4. The sternal reconstruction system of claim 3, wherein the end fitting member is constructed from a material comprising at least one of titanium, alloys of titanium, stainless steel and resorbable materials.

5. The sternal reconstruction system of claim 3, wherein the upper surface of the end fitting member has rounded edges.

6. The sternal reconstruction system of claim 3, wherein the lower surface of the end fitting member is flat.

7. The sternal reconstruction system of claim 1, wherein the fitting piece is a flattened cylindrical tube having a long cross-sectional axis and a short cross-sectional axis.

8. The sternal reconstruction system of claim 7, wherein the first and second ends of the fitting piece are parallel to each other.

9. The sternal reconstruction system of claim 7, wherein at least one side of the fitting piece has a long cross-sectional axis that is crimped along the length so as to provide a necked region that partially defines the first and second channels through the fitting piece.

10. The sternal reconstruction system of claim 9, wherein a second side of the fitting piece has a long cross-sectional axis L that is crimped along the length so as to provide a necked region that partially defines the first and second channels through the fitting piece, and the first and second channels each have the same size aperture and cross-section.

11. The sternal reconstruction system of claim 9, wherein each of the first and second channels has a diameter of from about 0.7 mm to about 2.5 mm.

12. The sternal reconstruction system of claim 9, wherein the fitting piece is crimped at a midpoint of the long cross-sectional axis along its length to form a necked region that partially defines the first and second channels.

13. The sternal reconstruction system of claim 7, wherein the fitting piece is from about 3 mm to about 15 mm in length, the long cross-sectional axis is from about 3 mm to about 8 mm, and the short cross-sectional axis is from about 1 mm to about 5 mm.

14. The sternal reconstruction system of claim 7, wherein the fitting piece is constructed from a material comprising at least one of, titanium, alloys of titanium, stainless steel and resorbable materials.

15. The sternal reconstruction system of claim 1, further comprising at least one cannulated screw.

16. The sternal reconstruction system of claim 15, wherein the at least one cannulated screw comprises at least one of a locking and a non-locking screw.

17. The sternal reconstruction system of claim 15, wherein the at least one cannulated screw is at least partially threaded for attachment to bone.

18. The sternal reconstruction system of claim 15, wherein the at least one cannulated screw is constructed from a material comprising at least one of titanium, alloys of titanium, stainless steel and resorbable materials.

19. The sternal reconstruction system of claim 15, wherein the at least one cannulated screw comprises a head which comprises a hollow aperture, wherein the hollow aperture is sized and shaped so as to accommodate the end fitting member.

20. The sternal reconstruction system of claim 1, wherein the fitting piece has a beveled portion at the first end of the fitting piece or the second end of the fitting piece, the lower surface being configured to abut the beveled portion of the fitting piece such that the end fitting member sits at least partially within one of the first and second channels.

21. The sternal reconstruction system of claim 1, wherein the fitting piece has a countersunk portion at the first end of the fitting piece or the second end of the fitting piece, the lower surface being configured to abut the countersunk portion of the fitting piece such that the end fitting member sits at least partially within one of the first and second channels.

22. The sternal reconstruction system of claim 1, wherein the fitting piece is configured to abut the end fitting member such that the end fitting member sits at least partially within one of the first and second channels.

23. The sternal reconstruction system of claim 1, wherein the fitting piece is crimpable to the flexible cable to secure the flexible cable to the fitting piece when the fitting piece is positioned adjacent the sternum and the second end of the flexible cable is passed at least partially through the first and second channels of the fitting piece.

24. A sternal reconstruction system configured to secure parts of a sternum, the system comprising:
    a flexible cable having first and second ends;
    an end fitting member attached to the first end of the flexible cable;
    a fitting piece having a first end, a second end, a length extending between the first end of the fitting piece and the second end of the fitting piece, and a first channel and a second channel each extending substantially parallel through the fitting piece along the length from the first end of the fitting piece to the second end of the fitting piece; and
    a ferrule including an outer surface and an inner surface radially opposite the outer surface, the inner surface defining a hole that extends through the ferrule along a central hole axis, the hole sized to receive the flexible cable, the outer surface circumferentially solid along a line that lies in a plane normal to the central hole axis, the ferrule including a sharp edge that extends from the inner surface into the hole such that the sharp edge is configured to cut the flexible cable as the ferrule is crimped onto the flexible cable when the flexible cable is disposed within the hole;
    wherein the fitting piece is configured to abut the end fitting member when the fitting piece is positioned adjacent the sternum and the second end of the flexible cable is passed at least partially through the first and second channels of the fitting piece.

25. The sternal reconstruction system of claim 24, wherein the length extends between the first end and the second end along a select direction, and each of the first and second channels is open to both the first end and the second end, and the first and second channels are open to each other along a direction perpendicular to the select direction; and
    wherein the end fitting member is sized to abut the fitting piece, and the fitting piece is configured to be directly securable to the flexible cable after the second end of the flexible cable has been passed through the first channel, looped around a sternal fracture, and passed at least partially through the second channel of the fitting piece.

26. The sternal reconstruction system of claim 25, wherein the at least one flexible cable is attached to a suture.

27. The sternal reconstruction system of claim 25, further comprising at least one cannulated screw.

28. The sternal reconstruction system of claim 27, wherein the at least one flexible cable is attached to a suture.

29. The sternal reconstruction system of claim 25, wherein the fitting piece has a beveled portion at the first end of the fitting piece or the second end of the fitting piece, the lower surface being configured to abut the beveled portion of the fitting piece such that the end fitting member sits at least partially within one of the first and second channels.

30. The sternal reconstruction system of claim 25, wherein the fitting piece has a countersunk portion at the first end of the fitting piece or the second end of the fitting piece, the lower surface being configured to abut the countersunk portion of the fitting piece such that the end fitting member sits at least partially within one of the first and second channels.

31. The sternal reconstruction system of claim 25, wherein the first and second channels of the at least one fitting piece each extend through the fitting piece parallel to each other.

32. The sternal reconstruction system of claim 25, wherein the end fitting member is configured to sit at least partially within one of the first and second channels.

33. The sternal reconstruction system of claim 24, wherein the fitting piece is a flattened cylindrical tube having a long cross-sectional axis and a short cross-sectional axis.

34. The sternal reconstruction system of claim 33, wherein the first and second ends of the fitting piece are parallel to each other.

35. The sternal reconstruction system of claim 24, wherein the fitting piece is crimped along the length so as to provide a necked region that partially defines the first and second channels.

36. The sternal reconstruction system of claim 24, wherein the first and second channels have the same size aperture and cross-section.

37. The sternal reconstruction system of claim 24, further comprising at least one cannulated screw.

38. The sternal reconstruction system of claim 37, wherein the at least one cannulated screw comprises at least one of a locking and a non-locking screw.

39. The sternal reconstruction system of claim 37, wherein the at least one cannulated screw is at least partially threaded for attachment to bone.

40. The sternal reconstruction system of claim 37, wherein the at least one cannulated screw comprises a head which comprises a hollow aperture, wherein the hollow aperture is sized and shaped so as to accommodate the end fitting member.

41. The sternal reconstruction system of claim 24, wherein the end fitting member defines a cross-sectional dimension greater than that of the flexible cable.

42. The sternal reconstruction system of claim 24, wherein the first and second channels are open to each other along a direction perpendicular to the length.

43. The sternal reconstruction system of claim 24, wherein the sternal reconstruction system defines an assembled configuration in which: 1) the end fitting member abuts the first end of the fitting piece at a first location aligned with the first channel, and 2) the ferrule is crimped to the flexible cable and abuts the second end of the fitting piece at a second location aligned with the second channel.

* * * * *